United States Patent [19]

Kucznierz et al.

[11] Patent Number: 6,037,334
[45] Date of Patent: Mar. 14, 2000

[54] PHOSPHONATES, PROCESS FOR PREPARING THE SAME AND MEDICAMENTS

[75] Inventors: Ralf Kucznierz, Bad Dürkheim; Herbert Leinert, Heppenheim; Wolfgang von der Saal, Weinheim; Richard Neidlein, Heidelberg; Christiane Kehr, Berlin, all of Germany

[73] Assignee: Roche Diagnostics GmbH, Mannheim, Germany

[21] Appl. No.: 09/297,089

[22] PCT Filed: Nov. 14, 1997

[86] PCT No.: PCT/EP97/06365

§ 371 Date: Jul. 15, 1999

§ 102(e) Date: Jul. 15, 1999

[87] PCT Pub. No.: WO98/22483

PCT Pub. Date: May 28, 1998

[30] Foreign Application Priority Data

Nov. 16, 1996 [EP] European Pat. Off. ............. 96118410

[51] Int. Cl.[7] .............................. C07F 9/59; C07F 9/572; C07F 9/553; A61K 31/675
[52] U.S. Cl. .................. 514/79; 514/89; 514/91; 514/277; 514/315; 514/336; 540/542; 546/22; 546/184; 546/192; 548/400; 548/413
[58] Field of Search .................. 514/79, 89, 91, 514/277, 315, 336; 546/22, 184, 192; 548/400, 413; 540/542

[56] References Cited

FOREIGN PATENT DOCUMENTS 0 540 051  3/1993  European Pat. Off. .
96 16940   6/1996  WIPO .

OTHER PUBLICATIONS

Chemical Abstracts, vol. 123,No. 21, Nov. 20, 1995, Ikeuchi et al., "Preparation of aromatic amidine derivatives as inhibitors of human blood coagulation factor for treatment and prevention . . . ".

Nagahara et al., "Dibasic (Amidinoaryl) propanoic Acid Derivatives as Novel Blood Coagulation Factor Xa Inhibitors", J. Med. Chem. 94; vol. 37 (8) pp. 1200–1207, Daiichi Pharmaceutical Company Ltd.

Primary Examiner—Mukund J. Shah
Assistant Examiner—Pavanaram K Sripada
Attorney, Agent, or Firm—Arent Fox Kintner Plotkin & Kahn, PLLC

[57] ABSTRACT

Compounds of formula I

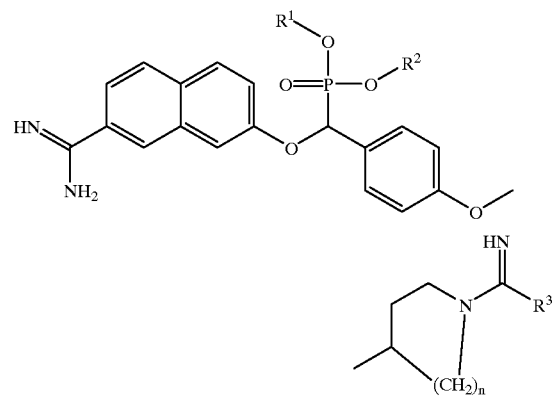

(I)

in which $R_1$, $R^2$ are the same or different and denote a hydrogen atom, an alkyl group, a cycloalkyl group, a hydroxyalkyl group, an alkenyl group, an alkinyl group or an aralkyl group or $R^1$ and $R^2$ together denote an alkylene residue which, together with the bound oxygen atoms and the phosphorus atom carrying the oxygen atoms, forms a saturated 5-membered to 8-membered ring;

$R^3$ denotes an optionally substituted amino group, an alkyl group, a cycloalkyl residue or an optionally substituted aryl residue;

n denotes an integer between 1 and 4, as well as hydrates, solvates and physiologically tolerated salts thereof, their optically active forms, processes for their production as well as pharmaceutical preparations having factor Xa-inhibitory properties which contain these compounds.

12 Claims, No Drawings

PHOSPHONATES, PROCESS FOR PREPARING THE SAME AND MEDICAMENTS

This application is a 371 of PCT/EP97/06365 filed Nov. 14, 1997.

The invention concerns new phosphonates of the general formula I

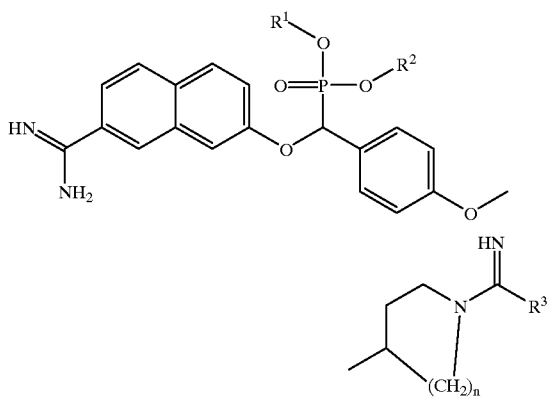

(I)

in which
R$^1$, R$^2$ are the same or different and denote a hydrogen atom, an alkyl group, a cycloalkyl group, a hydroxyalkyl group, an alkenyl group, an alkinyl group or an aralkyl group or R$^1$ and R$^2$ together denote an alkylene residue which, together with the bound oxygen atoms and the phosphorus atom carrying the oxygen atoms, forms a saturated 5-membered to 8-membered ring;
R$^3$ denotes an optionally substituted amino group, an alkyl group, a cycloalkyl residue or an optionally substituted aryl residue;
n denotes an integer between 1 and 4,
as well as hydrates, solvates and physiologically tolerated salts thereof. The invention also concerns the optically active forms, racemates and mixtures of diastereomers of these compounds.

The invention also concerns processes for the production of the above-mentioned compounds, pharmaceutical preparations that contain such compounds as well as the use of these compounds in the production of pharmaceutical preparations.

The phosphonates of the general formula I, their solvates and their salts intervene in the process of blood coagulation by the reversible inhibition of factor Xa and thus they prevent formation of hyaline thrombi. They can therefore be used to combat and prevent diseases such as thrombosis, apoplexy, coronary infarction, inflammations and arteriosclerosis.

Factor Xa is a serine protease of the coagulation system which catalyses the proteolytic conversion of prothrombin into thrombin. Thrombin as the last enzyme of the coagulation cascade on the one hand cleaves fibrinogen to form fibrin which becomes an insoluble gel after cross-linking by factor XIIIa and forms the matrix for a thrombus; on the other hand thrombin activates platelet aggregation by proteolysis of its receptor on the blood platelets and in this way also contributes to thrombus formation. When a blood vessel is damaged these processes are necessary in order to stop bleeding. No measurable thrombin concentrations are present in blood plasma under normal conditions. An increase in the thrombin concentration can lead to the formation of thrombi and hence to thromboembolic diseases which occur very frequently above all in industrial countries. The formation of thrombin can be prevented by inhibiting factor Xa.

It has recently been reported that amidinoarylpropanoic acid derivatives such as (+)-(2S)-2-[4-[[(3S)-1-acetimidoyl-3-pyrrolidinyl]oxy]phenyl]3-3-(7-amidino-2-naphthyl] propanoic acid-hydrochloride-pentahydrate (DX-9065a; formula IIa) inhibit factor Xa (*J. Med. Chem.* 1994, 37, 1200–1207; Thrombosis and Haemostasis 1994, 71, 314–319; EP-0-540-051-A-1). Further known factor Xa inhibitors are 1,2-bis-(5-amidino-2-benzofuranyl)-ethane (DABE, formula IIb; *Thrombosis Research* 1980, 19, 339–349) and also phenyl-amino-methyl-naphthamidines of the general formula IIc (WO96/16940).

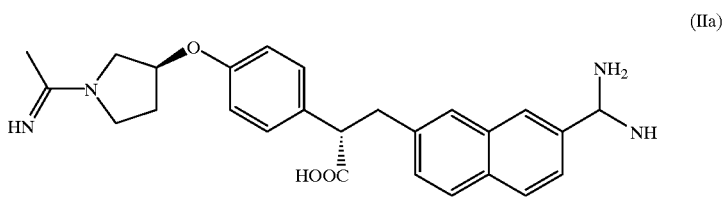

(IIa)

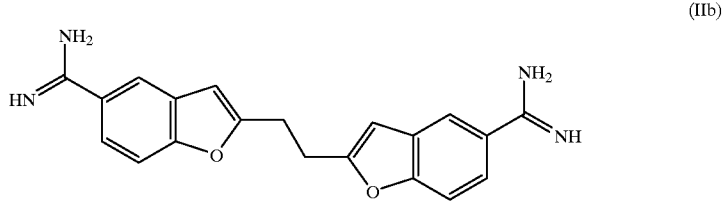

(IIb)

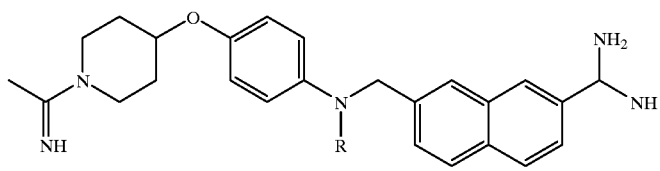

(IIc)

The new phosphonates according to the invention of the general formula I as well as hydrates, solvates and physiologically tolerated salts thereof are potent and selective factor Xa inhibitors.

In the general formula I the substituents $R^1$ and $R^2$ can be the same or different.

If $R^1$, $R^2$ in the general formula I denote an alkyl group, this can be straight-chained or branched and contain 1 to 6 carbon atoms. A methyl, ethyl, n-propyl, i-propyl, n-butyl, i-butyl, t-butyl, pentyl and hexyl group are preferred.

If $R^1$, $R^2$ in the general formula I denote a cycloalkyl group, this can be substituted or unsubstituted and contain 3 to 8 carbon atoms. A cyclopropyl, cyclopentyl, cyclohexyl and cyclooctyl group are preferred.

If $R^1$, $R^2$ in the general formula I denote a hydroxyalkyl group, this can be straight-chained or branched and contain 1 to 6 carbon atoms. A hydroxymethyl, hydroxyethyl, hydroxypropyl, hydroxybutyl, hydroxypentyl and hydroxyhexyl group are preferred.

If $R^1$, $R^2$ in the general formula I denote an alkenyl group, this can be straight-chained or branched and contain 2 to 6 carbon atoms. A vinyl, 1-propenyl, 2-propenyl, 2-methyl-2-propenyl, 1-butenyl, 1-pentenyl and 1-hexenyl group are preferred.

If $R^1$, $R^2$ in the general formula I denote an alkinyl group, this can be straight-chained or branched and contain 2 to 6 carbon atoms. An ethinyl and propargyl group are preferred.

If $R^1$, $R^2$ in the general formula I denote an aralkyl group, this contains a phenyl group linked to a straight-chained or branched $C_1$–$C_6$ alkyl chain, a naphthyl group linked to a straight-chained or branched $C_1$–$C_6$ alkyl chain or a biphenyl group linked to a straight-chained or branched $C_1$–$C_6$ alkyl chain. In this case a benzyl group, a p-phenylbenzyl group and a naphthylmethyl group are preferred.

If $R^1$, $R^2$ in the general formula I together denote an alkylene group, this can be straight-chained or branched and contain 2 to 6 carbon atoms. An ethylene, propylene and 2,3-dimethyl-2,3-butanediyl group are preferred.

If $R^3$ in the general formula I denotes an amino group, this can be unsubstituted or substituted with one or two $C_1$–$C_6$ alkyl groups preferably methyl or ethyl, with one or two $C_3$–$C_8$ cycloalkyl groups preferably cyclopropyl, cyclopentyl, cyclohexyl or cyclooctyl, with one or two $C_1$–$C_6$ hydroxyalkyl groups preferably hydroxyethyl or hydroxypropyl, with one or two $C_3$–$C_6$ alkenyl groups preferably allyl, with one or two $C_3$–$C_6$ alkinyl groups preferably propargyl or with one or two aralkyl groups preferably benzyl. In this case the specification ($C_1$–$C_6$) represents a straight-chained or branched alkyl chain with 1 to 6 carbon atoms, ($C_3$–$C_8$) represents a branched or unbranched cycloalkyl group with 3 to 8 carbon atoms and ($C_3$–$C_6$) represents either a branched or unbranched alkenyl or alkinyl group with 3 to 6 carbon atoms.

If $R^3$ in the general formula I denotes an alkyl group, this can be straight-chained or branched and contain 1 to 6 carbon atoms. A methyl, ethyl, n-propyl, i-propyl, n-butyl, i-butyl, t-butyl, pentyl and hexyl group are preferred.

If $R^3$ in the general formula I denotes a cycloalkyl group, this can be branched or unbranched and contain 3 to 8 carbon atoms. A cyclopropyl, cyclopentyl, cyclohexyl and cyclooctyl group are preferred.

If $R^3$ in the general formula I denotes an aryl residue this is understood to include a phenyl, biphenyl or naphthyl group. The aryl residue can be unsubstituted or optionally carry one or several $C_1$–$C_6$ alkyl preferably methyl, $C_1$–$C_6$ alkyloxy preferably methoxy or halogen substituents. In this case the specification ($C_1$–$C_6$) represents a straight-chained or branched alkyl chain with 1 to 6 carbon atoms. Halogens as substituents of the aryl residue can be fluorine, chlorine, bromine and iodine atoms, but preferably chlorine or bromine atoms.

The number n denotes an integer between 1 and 4.

Compounds of the general formula I are preferred in which $R^1$, $R^2$ are the same or different and denote a hydrogen atom, a methyl group, an ethyl group, a propyl group, an allyl group, a propargyl group or a benzyl group or $R^1$ and $R^2$ together denote an ethylene group or a propylene group;

$R^3$ denotes an amino group, an N-methyl-amino group, an N-benzyl-amino group, an N-allyl-amino group, an N,N-dimethylamino group, a methyl group, an ethyl group, a cyclopropyl group or a 4-methoxyphenyl residue and n can be 1 or 2.

Compounds of the general formula I are particularly preferred in which $R^1$ and $R^2$ are the same and denote an ethyl group;

$R^3$ denotes a methyl group and n denotes the number 2.

Physiologically tolerated salts of the general formula I are understood as for example formates, acetates, caproates, oleates, lactates or salts of carboxylic acids with up to 18 carbon atoms or salts of dicarboxylic acids and tricarboxylic acids such as citrates, malonates and tartrates or alkanesulfonates with up to 10 carbon atoms or p-toluenesulfonates or salicylates or trifluoroacetates or salts of physiologically tolerated mineral acids such as hydrochloric acid, hydrobromic acid, hydroiodic acid, sulphuric acid, phosphoric acid. The compounds of formula I with one or two free acid groups on the phosphonate fragment can also form salts with physiologically tolerated bases. Examples of such salts are alkaline metal, alkaline-earth metal, ammonium and alkylammonium salts such as a sodium, potassium, calcium or tetramethylammonium salt.

The compounds of formula I can be solvated and in particular hydrated. The hydration can be achieved in the course of the production process or gradually occur as a result of hygroscopic properties of a compound of formula I which is firstly anhydrous.

The invention also concerns the optically active forms, the racemates and mixtures of diastereomers of compounds of the general formula I.

For the production of pharmaceutical preparations, the substances of the general formula I are mixed with suitable pharmaceutical carrier substances, aromatics, flavourings and dyes and are for example formed into tablets or dragées or are suspended or dissolved in water or oil e.g. olive oil with the addition of appropriate auxiliary substances.

The substances of the general formula I and their salts can be administered enterally or parenterally in a liquid or solid form. Water is preferably used as an injection medium which contains the usual additives for injection solutions such as stabilizers, solubilizers or buffers. Such additives are e.g. tartrate and citrate buffer, complexing agents (such as ethylenediaminetetraacetic acid and their non-toxic salts) and high molecular polymers such as liquid polyethylene oxide in order to regulate viscosity. Solid carrier materials are e.g. starch, lactose, mannitol, methylcellulose, talcum, highly dispersed silicic acids, high molecular fatty acids (such as stearic acid), animal and vegetable fats and solid high molecular polymers (such as polyethylene glycols). Preparations suitable for oral administration can, if desired, contain flavourings and sweeteners.

The compounds are usually administered in amounts of 10–1500 mg per day in relation to 75 kg body weight. It is preferable to administer 1–2 tablets with a content of active substance of 5–500 mg 2–3 times per day. The tablets can also be retarded as a result of which only 1–2 tablets with 20–700 mg active substance have to be administered per day. The active substance can also be administered by injection 1–8 times per day or by continuous infusion in which case 50–2000 mg per day are usually sufficient.

Compounds of the general formula I are produced according to known methods.

Compounds of the general formula I are produced by for example reacting a compound of the general formula III

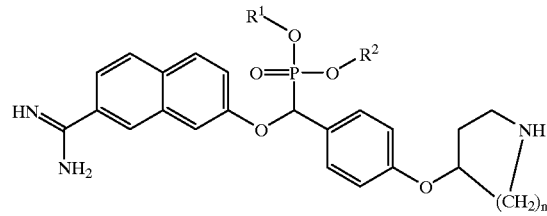

(III)

in which $R^1$, $R^2$ and n have the meanings stated above, with a guanylation reagent such as 1H-pyrazole-1-carboxamidine or S-methylisothiourea in an inert solvent such as e.g. dimethylformamide, dioxane, dimethylsulfoxide or toluene at temperatures between 0° C. and the boiling point of the solvent, preferably at 0 to 30° C. in the presence of an auxiliary base such as e.g. triethylamine, N-methylmorpholine, pyridine or ethyldiisopropylamine.

Compounds of the general formula I can also be produced by reacting compounds of the general formula III, in which $R^1$, $R^2$ and n have the meanings given above, with appropriately substituted guanylation reagents in an inert solvent such as e.g. dimethylformamide, dioxane, dimethylsulfoxide or toluene at temperatures between 0° C. and the boiling point of the solvent, preferably at 0 to 30° C. in the presence of an auxiliary base such as e.g. triethylamine, N-methylmorpholine, pyridine or ethyldiisopropylamine.

Compounds of the general formula I can also be produced by reacting compounds of the general formula III, in which $R^1$, $R^2$ and n have the meanings given above, with aliphatic or aromatic imidic acid ester hydrochlorides in an inert solvent such as tetrahydrofuran, diethyl ether, ethanol, dimethylformamide or dioxane in the presence of an auxiliary base such as triethylamine, ethyldiisopropylamine or N-methylmorpholine.

Compounds of the general formula III are produced by reacting a compound of the general formula IV,

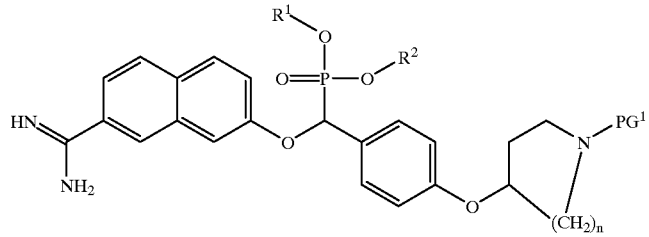

(IV)

in which $R^1$, $R^2$ and n have the meanings stated above and $PG^1$ denotes a protective group such as e.g. a benzyloxycarbonyl group, a t-butyloxycarbonyl group or an allyloxycarbonyl group, with a protective group cleaving reagent. Protective groups are cleaved according to conventional methods (see e.g. T. W. Green, P. G. M. Wuts, Protective Groups in Organic Synthesis, 2nd ed., John Wiley and Sons Inc. 1991) by acidic reagents such as e.g. hydrogen bromide in glacial acetic acid or trifluoroacetic acid or etherial HCl solution or hydrogenolytically or by palladium-catalysed or rhodium-catalysed cleavage.

Compounds of the general formula IV are produced by reacting a compound of the general formula V, (V)

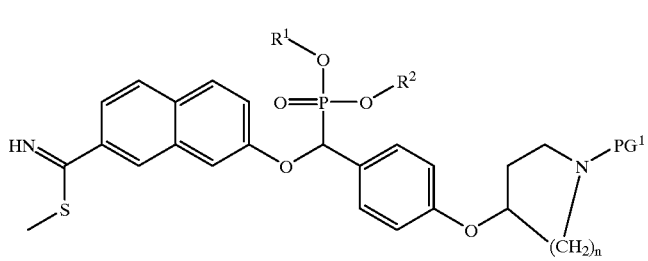

in which $R^1$, $R^2$, n and $PG^1$ have the meanings stated above with ammonia or ammonium salts such as e.g. ammonium acetate, ammonium chloride or ammonium oxalate in an inert solvent such as methanol, ethanol or isopropanol at temperatures between 0° C. and the boiling point of the solvent, preferably between room temperature and 65° C.

Compounds of the general formula V are produced by reacting a compound of the general formula VI, (VI)

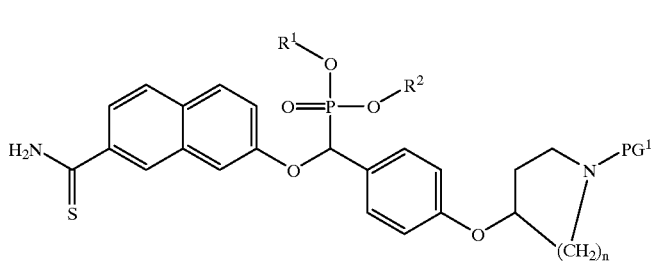

in which $R^1$, $R^2$, n and $PG^1$ have the meanings stated above, with methylation reagents such as methyl iodide or dimethyl sulfate in an inert solvent such as methanol, ethanol, acetone or dioxane at temperatures between 0° C. and the boiling point of the solvent, preferably between room temperature and 55° C.

Compounds of the general formula VI are obtained by treating a compound of the general formula VII, (VII)

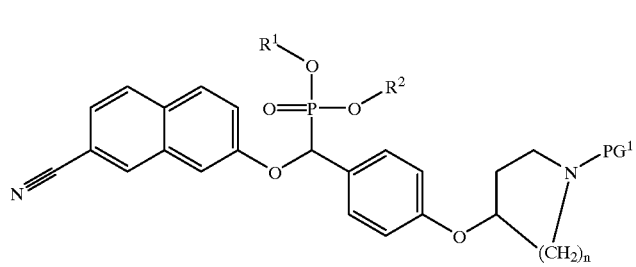

in which $R^1$, $R^2$, n and $PG^1$ have the meanings stated above, with hydrogen sulfide in an inert solvent such as pyridine, methanolic ammonia solution, ethanol, chloroform or dimethylformamide at temperatures between 0° C. and the boiling point of the solvent, preferably between 0° C. and room temperature optionally in the presence of an auxiliary base such as diethylamine, triethylamine, ethyldiisopropylamine or N-methylmorpholine.

Compounds of the general formula VII are produced by condensing 7-hydroxynaphthalene-2-carbonitrile with a compound of the general formula VIII,

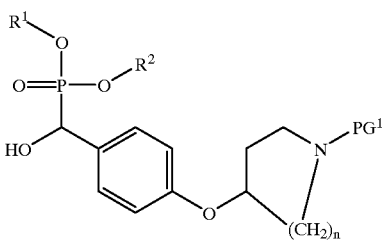

(VIII)

in which $R^1$, $R^2$, n and $PG^1$ have the meanings stated above, in an inert solvent such as dioxane, tetrahydrofuran or toluene in the presence of diethylazodicarboxylate and triphenylphosphine, trimethyl or triethylphosphite at temperatures between 0 and 50° C., preferably at room temperature.

7-Hydroxy-naphthalene-2-carbonitrile is known in the literature (see e.g. L. M. Tolbert, J. E. Haubrich, *J. Am. Chem. Soc.* 1994, 116, 10593–10600) and can be prepared by the processes described therein or in other references (e.g: S. A. Jacobs, R. G. Harvey, *J. Org. Chem.* 1983, 48, 5134–5135; V. N. Kopranenkov, E. A. Makarova, E. A. Luk'yanets, *Zh. Org. Khim.* 1981, 358–361; B. Basu, D. Mukherjee, *J. Chem. Soc. Chem. Commun.* 1984, 105–106; B. Basu, D. Mukherjee, *Tetrahedon Lett.* 1984, 4445–4446; S. K. Maity, D. Mukherjee, *Tetrahedron Lett.* 1983, 5919–5920).

Compounds of the general formula VIII are produced by reacting a compound of the general formula IX,

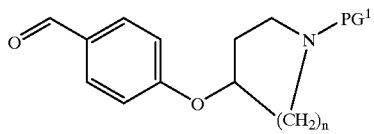

(IX)

in which n and $PG^1$ have the meanings stated above with a compound of the general formula X,

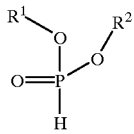

(X)

in which $R^1$ and $R^2$ have the meanings stated above in the presence of an auxiliary base such as triethylamine, diisopropylethylamine, N-methylmorpholine, pyridine, sodium methylate or sodium ethylate at temperatures between 0° C. and 80° C., preferably at 60° C.

Compounds of the general formula X, in which $R^1$ and $R^2$ have the meanings stated above, are either commercially available or known in the literature or can be synthesized by standard methods from commercial precursors or precursors known in the literature.

Compounds of the general formula IX are produced by condensing a compound of the general formula XI,

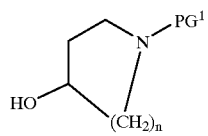

(XI)

in which n and $PG^1$ have the meanings stated above, with 4-hydroxybenzaldehyde in an inert solvent such as dioxane, tetrahydrofuran or toluene in the presence of diethylazodicarboxylate and triphenylphosphine, trimethylphosphite or triethylphosphite at temperatures between 0 and 50° C., preferably at room temperature.

Compounds of the general formula XI in which n and $PG^1$ have the meanings stated above are either commercially available or known in the literature or can be produced according to processes known from the literature (see e.g. K. L. Bhat, D. M. Flanagan, M. M. Jouillé, *Synth. Commun.* 1985, 15, 587–598; P. G. Houghton, G. R. Humphrey, D. J. Kennedy, D. C. Roberts, S. H. Wright, *J. Chem. Soc. Perkin Trans.*1 1993, 13, 1421–1424; T. W. Green, P. G. M. Wuts, Protective Groups in Organic Synthesis, 2nd ed., John Wiley and Sons Inc. 1991).

Certain compounds of the general formula I can be subsequently converted into other compounds of the general formula I.

This applies to compounds of the general formula I in which n and $PG^1$ have the meanings stated above and $R^1$ and $R^2$ are the same or different and denote an alkyl group, a cycloalkyl group, an alkenyl group, an alkynyl group or an aralkyl group. These compounds can be converted into compounds of the general formula I with a free phosphonic acid group by partial hydrolysis e.g. with aqueous potassium hydroxide solution, with aqueous pyridine or by treatment with sodium iodide in acetone at temperatures between 0° C. and the boiling point of the solvent, preferably at reflux temperature.

This also applies to compounds of the general formula I in which n and $PG^1$ have the meanings stated above, $R^1$ denotes an alkyl group or a cycloalkyl group and $R^2$ denotes a benzyl group. In this process the benzyl group is replaced by a hydrogen atom by catalytic hydrogenation in inert solvents such as methanol, ethanol, tetrahydrofuran or dioxane in the presence of a catalyst preferably palladium on carbon. The benzyl group can also be removed by reaction with a strong acid such as trifluoroacetic acid in the presence of mesitylene, anisole or thioanisole at temperatures between 0 and 50° C., preferably at room temperature or by treatment with Lewis acids such as $BF_3$ etherate in an inert solvent such as toluene, acetonitrile, diethyl ether or tetrahydrofuran at temperatures between 0° C. and the boiling point of the solvent, preferably between room temperature and the boiling point of the solvent.

This also applies to compounds of the general formula I in which n and $PG^1$ have the meanings stated above, $R^1$ denotes an alkyl group or a cycloalkyl group and $R^2$ denotes an allyl group. In this process the allyl group is replaced by a hydrogen atom by transition metal catalysed cleavage for example in the presence of a rhodium catalyst such as tris-triphenylphosphine rhodium chloride or a palladium catalyst such as tetrakis-triphenylphosphine palladium in an inert solvent such as tetrahydrofuran or dioxane optionally in the presence of a nucleophile such as malonic acid diethyl ester, tributyl tin hydride, 5,5-dimethylcyclohexane-1,3-dione or piperidine at temperatures between 0° C. and 50° C., preferably at room temperature.

This also applies compounds of the general formula I in which n and PG¹ have the meanings stated above and $R^1$ and $R^2$ are the same or different and denote an alkyl group, a cycloalkyl group, a hydroxyalkyl group, an alkenyl group, an alkinyl group or an aralkyl group. These compounds can be converted into free phosphonic acids of the general formula I by treatment with trimethylsilyl iodide or trimethylsilyl bromide at temperatures between 0° C and the boiling point of the solvent, preferably between room temperature and 50° C. in an inert solvent such as diethyl ether, tetrahydrofuran, dimethylformamide, dichloromethane or chloroform. The phosphonic acid esters of the general formula I can also be completely saponified by acid hydrolysis in an aqueous medium for example in dilute or semiconcentrated hydrochloric acid at temperatures between room temperature and the boiling point of the reaction medium preferably at reflux temperature.

Pure enantiomers of compounds of formula I are produced either by racemate resolution (via salt formation with optically active acids or bases) or by using optically active starting materials in the synthesis or by enzymatic hydrolysis.

The following compounds are preferred within the sense of the invention in addition to those mentioned in the examples:

1. ((7-Carbamimidoyl-naphthalen-2-yloxy)-{4-[1(1-imino-ethyl)-piperidin-4-yloxy]-phenyl}-methyl)-phosphonic acid diallyl ester
2. {(7-Carbamimidoyl-naphthalen-2-yloxy)-[4-(1-carbamimidoyl-piperidin-4-yloxy)-phenyl]-methyl}-phosphonic acid diethyl ester
3. ((7-Carbamimidoyl-naphthalen-2-yloxy)-{4-[1-(1-imino-ethyl)-pyrrolidin-3-yloxy]-phenyl}-methyl)-phosphonic acid diethyl ester
4. {(7-Carbamimidoyl-naphthalen-2-yloxy)-[4-(1-carbamimidoyl-pyrrolidin-3-yloxy)-phenyl]-methyl}-phosphonic acid diethyl ester
5. ((7-Carbamimidoyl-naphthalen-2-yloxy)-{4-[1-(1-imino-ethyl)-piperidin-4-yloxy]-phenyl}-methyl)-phosphonic acid monoethyl ester
6. {(7-Carbamimidoyl-naphthalen-2-yloxy)-[4-(1-carbamimidoyl-piperidin-4-yloxy)-phenyl]-methyl}-phosphonic acid monoethyl ester
7. ((7-Carbamimidoyl-naphthalen-2-yloxy)-{4-[1-(1-imino-ethyl)-pyrrolidin-3-yloxy]-phenyl}-methyl)-phosphonic acid monoethyl ester
8. {(7-Carbamimidoyl-naphthalen-2-yloxy)-[4-(1-carbamimidoyl-pyrrolidin-3-yloxy)-phenyl]-methyl}-phosphonic acid monoethyl ester
9. ((7-Carbamimidoyl-naphthalen-2-yloxy)-{4-[1-(1-imino-propyl)-piperidin-4-yloxy]-phenyl}-methyl)-phosphonic acid monoethyl ester
10. ((7-Carbamimidoyl-naphthalen-2-yloxy)-{4-[1-(1-imino-ethyl)-piperidin-4-yloxy]-phenyl}-methyl)-phosphonic acid
11. {(7-Carbamimidoyl-naphthalen-2-yloxy)-[4-(1-carbamimidoyl-piperidin-4-yloxy)-phenyl]-methyl}-phosphonic acid
12. ((7-Carbamimidoyl-naphthalen-2-yloxy)-{4-[1-(1-imino-ethyl)-pyrrolidin-3-yloxy]-phenyl}-methyl)-phosphonic acid
13. {(7-Carbamimidoyl-naphthalen-2-yloxy)-[4-(1-carbamimidoyl-pyrrolidin-3-yloxy)-phenyl]-methyl}-phosphonic acid
14. ((7-Carbamimidoyl-naphthalen-2-yloxy)-{4-[1-(1-imino-ethyl)-piperidin-4-yloxy]-phenyl}-methyl)-phosphonic acid dimethyl ester
15. {(7-Carbamimidoyl-naphthalen-2-yloxy)-[4-(1-carbamimidoyl-piperidin-4-yloxy)-phenyl]-methyl}-phosphonic acid dimethyl ester
16. ((7-Carbamimidoyl-naphthalen-2-yloxy)-{4-[1-(1-imino-ethyl)-pyrrolidin-3-yloxy]-phenyl}-methyl)-phosphonic acid dimethyl ester
17. {(7-Carbamimidoyl-naphthalen-2-yloxy)-[4-(1-carbamimidoyl-pyrrolidin-3-yloxy)-phenyl]-methyl}-phosphonic acid dimethyl ester
18. ((7-Carbamimidoyl-naphthalen-2-yloxy)-{4-[1-(1-imino-ethyl)-piperidin-4-yloxy]-phenyl}-methyl)-phosphonic acid monomethyl ester
19. {(7-Carbamimidoyl-naphthalen-2-yloxy)-[4-(1-carbamimidoyl-piperidin-4-yloxy)-phenyl]-methyl}-phosphonic acid monomethyl ester
20. ((7-Carbamimidoyl-naphthalen-2-yloxy)-{4-[1-(1-imino-ethyl)-pyrrolidin-3-yloxy]-phenyl}-methyl)-phosphonic acid monomethyl ester
21. {(7-Carbamimidoyl-naphthalen-2-yloxy)-[4-(1-carbamimidoyl-pyrrolidin-3-yloxy)-phenyl]-methyl}-phosphonic acid monomethyl ester
22. ((7-Carbamimidoyl-naphthalen-2-yloxy)-{4-[1-(1-imino-propyl)-piperidin-4-yloxy]-phenyl}-methyl)-phosphonic acid monomethyl ester
23. ((7-Carbamimidoyl-naphthalen-2-yloxy)-{4-[1(1-imino-ethyl)-piperidin-4-yloxy]-phenyl}-methyl)-phosphonic acid dipropyl ester
24. ((7-Carbamimidoyl-naphthalen-2-yloxy)-[4-(1-carbamimidoyl-piperidin-4-yloxy)-phenyl]-methyl}-phosphonic acid dipropyl ester
25. ((7-Carbamimidoyl-naphthalen-2-yloxy)-{4-[1-(1-imino-ethyl)-pyrrolidin-3-yloxy]-phenyl}-methyl)-phosphonic acid dipropyl ester
26. {(7-Carbamimidoyl-naphthalen-2-yloxy)-[4-(1-carbamimidoyl-pyrrolidin-3-yloxy)-phenyl]-methyl}-phosphonic acid dipropyl ester
27. ((7-Carbamimidoyl-naphthalen-2-yloxy)-{4-[1-(1-imino-ethyl)-piperidin-4-yloxy]-phenyl}-methyl)-phosphonic acid dibenzyl ester
28. {(7-Carbamimidoyl-naphthalen-2-yloxy)-[4-(1-carbamimidoyl-piperidin-4-yloxy)-phenyl]-methyl}-phosphonic acid dibenzyl ester
29. ((7-Carbamimidoyl-naphthalen-2-yloxy)-{4-[1-(1-imino-ethyl)-pyrrolidin-3-yloxy]-phenyl}-methyl)-phosphonic acid dibenzyl ester
30. {(7-Carbamimidoyl-naphthalen-2-yloxy)-[4-(1-carbamimidoyl-pyrrolidin-3-yloxy)-phenyl]-methyl}-phosphonic acid dibenzyl ester

EXAMPLE 1

(7-Carbamimidoyl-naphthalen-2-yloxy)-[{4-[1-(1-imino-ethyl)-piperidin-4-yloxy]-phenyl}-methyl)-phosphonic acid diethyl ester-dihydrochloride 1. 4-(4-Formyl-phenoxy)-piperidine-l-carboxylic acid tert-butyl ester A solution of 4.9 g (0.040 mol) 4-hydroxy-benzaldehyde, 10.0 g (0.050 mol) 4-hydroxy-piperidine-1-carboxylic acid tert-butyl ester (analogously to K. L. Bhat, D. M. Flanagan, M. M. Jouillé, *Synth. Commun.* 1985, 15, 587–598) and 13.1 g (0.050 mol) triphenylphosphine in 200 ml tetrahydrofuran is mixed at 5° C. with 7.9 ml (0.050 mol) azodicarboxylic acid diethyl ester and stirred for 24 hours at room temperature. After concentration the residue is purified by chromatography on a silica gel column (mobile solvent: isohexane/ethyl acetate 8:2, 7:3). After concentrating the appropriate column fractions one obtains 18.4 g (85%) of the title compound as a yellowish solid substance. Melting point. 63–64° C.; EI-MS: 305 (M⁺).

2. 4-{4-Diethoxy-phosphoryl)-hydroxy-methyl]-phenoxy}-piperidine-1-carboxylic acid tert.-butyl ester A mixture of 0.99 g (0.032 mol) 4-(4-formyl-phenoxy)-piperidine-1-carboxylic acid tert.-butyl ester, 0.46 ml (0.0036 mol) diethylphosphite and 0.50 ml triethylamine (0.0036 mol) is heated for 4 hours to 60° C. After concentration the residue is purified by chromatography on a silica gel column (mobile solvent: ethyl acetate/methanol 19:1). After concentrating the appropriate column fractions one obtains 1.40 g (97%) of the title compound as a viscous, colourless oil. $^{31}$P-NMR: $\delta$=23.2 ppm; EI-MS (silylated): 515 (M⁺-H+(CH$_3$)$_3$Si).

3. 4-{4-[(7-Cyano-naphthalen-2-yloxy)-(diethoxy-phosphoryl)-methyl]-phenoxy}-piperidine-1-carboxylic acid tert.-butyl ester A solution of 1.50 g (0.0088 mol) 7-hydroxy-naphthalene-2-carbonitrile, 3.93 g (0.0088 mol) 4-{4-[(diethoxy-phosphoryl)-hydroxy-methyl]-phenoxy}-piperidine-1-carboxylic acid tert.-butyl ester and 3.73 g (0.0142 mol) triphenylphosphine in 150 ml tetrahydrofuran is admixed at 5° C. with 2.23 ml (0.0142 mol) azodicarboxylic acid diethyl ester and stirred for 96 h at room temperature. After concentration the residue is purified by chromatography on a silica gel column (mobile solvent: ethyl acetate/methanol 19:1). After concentrating the appropriate column fractions one obtains 2.47 g (47%) of the title compound as a viscous, yellow oil. $^{31}$P-NMR: $\delta$=19.0 ppm.

4. 7-{[4-(1-tert-butoxycarbonyl-piperidin-4-yloxy)-phenyl]-diethoxy-phosphoryl)}-methyloxy-naphthalene-2-carbothioamide A solution of 1.61 g (0.0027 mmol) 4-{4-[(7-cyano-naphthalen-2-yloxy)-(diethoxy-phosphoryl)-methyl]-phenoxy}-piperidine-1-carboxylic acid tert.-butyl ester and 0.75 ml (0.0054 mmol) triethylamine in 15 ml pyridine is saturated with hydrogen sulfide. It is stirred for 2 days at room temperature, all volatile components are removed in a vacuum and 1.67 g (98%) of the title compound is obtained as an orange-coloured solid. 31P-NMR: $\delta$=19.5 ppm; (–)-FAB-MS: 627 (M-H⁺).

5. 7-{[4-(1-Tert-butoxycarbonyl-piperidin-4-yloxy)-phenyl]-(diethoxy-phosphoryl)}-methyloxy-naphthalene-2-carbimidothionic acid methyl ester hydroiodide A solution of 1.56 g (0.0025 mol) 7-{[4-(1-tert-butoxycarbonyl-piperidin-4-yloxy)-phenyl]-(diethoxy-phosphoryl)}-methyloxy-naphthalen-2-carbothioamide in 15 ml acetone is admixed with 0.77 ml (0.012 mol) methyl iodide and stirred for 24 h at room temperature in the absence of light. All volatile components are removed in a vacuum and 2.38 g of the title compound is obtained as a yellow solid ($^{31}$P-NMR: $\delta$=19.2 ppm). The crude product is reacted further without purification.

6. 7-{[4-(Piperidin-4-yloxy)-phenyl]-(diethoxy-phosphoryl)}-methyloxy-naphthalene-2-carbamidine-dihydrochloride A mixture of 2.27 g (0.003 mmol) 7-{[4-(1-tert-butoxycarbonyl-piperidin-4-yloxy)-phenyl]-(diethoxy-phosphoryl)}-methyloxy-naphthalene-2-carbimidothionic acid methyl ester hydroiodide and 0.68 g (0.0089) ammonium acetate in 20 ml methanol is heated for 24 hours under reflux. After cooling the reaction mixture 20 ml of a diethyl ether solution saturated with hydrogen chloride is added dropwise within 4 h while cooling on ice. After removing the solvent in a vacuum the residue is dissolved in 25 ml water, adjusted to pH 3 with 2 N HCl and chromatographed by means of preparative HPLC (RP-18 column, 15–25 μm) (mobile solvent: H$_2$O/CH$_3$OH 55:45, pH 3). After concentrating the appropriate column fractions and drying in a vacuum (10⁻² Torr), the residue is dissolved in 5 ml water/tert-butanol mixture (1:1) and lyophilised. 0.66 g (0.0011 mol) of the title compound with a melting point of 278° C. is obtained as a pale pink coloured solid. $^{31}$P-NMR: $\delta$=19.2 ppm; (+)-FAB-MS: 512 (M+H⁺).

7. ((7-Carbamididoyl-naphthalen-2-yloxy)-{4-[1-(1-imino ethyl)-piperidin-4-yloxy]-phenyl}-methyl)-phosphonic acid diethyl ester dihydrochloride 0.24 ml (1.71 mol) triethylamine is added dropwise under nitrogen at 5° C. to 42 mg acetimidic acid ethyl ester hydrochloride (0.34 mmol) and 100 mg 7-{[4-(piperidin-4-yloxy)-phenyl]-(diethoxy-phosphoryl)}-methyloxy-naphthalene-2-carbamidine-dihydrochloride (0.17 mmol) in 10 ml ethanol. It is stirred for 2 days at room temperature, concentrated by evaporation, the residue is dissolved in 10 ml water, it is adjusted to pH 3 with 2 N HCl and filtered. The filtrate is chromatographed by means of preparative HPLC (RP-18 column, 15–25 μm) (mobile solvent: H$_2$O, pH 3;

H$_2$O/CH$_3$CN 65:35, pH 3). After concentrating the appropriate column fractions and drying in a vacuum (10⁻² Torr) 70 mg (0.11 mmol; 65%) of the title compound is obtained as a bright, solidified oil. (+)-FAB-MS:553 (MH⁺).

EXAMPLE 2

Description of Pharmacological Experiments

Obtaining Plasma 9 parts of fresh blood from healthy donors was mixed with one part of sodium citrate solution (0.11 mol/l) and it was centrifuged for 10 minutes at room temperature at ca. 3000 r.p.m. The plasma was removed by pipette and can be stored at room temperature for ca. 8 hours.

Activated Partial Thromboplastin Time (APTT)

100 μl citrate plasma and 100 μl APTT reagent (Stago Diagnostics/Boehringer Mannheim GmbH; contains cephalin lyophilisate with a microcrystalline kieselguhr activator) are incubated for 3 minutes at 37° C. together with 10 μl dimethylsulfoxide (DMSO) or 10 μl of a solution of the active substance in DMSO in a ball coagulometer (KC10 from the Amelung Company). On addition of 100 μl 0.025 M calcium chloride solution a stopwatch is started and the time at which coagulation starts is determined. The APTT is ca. 28–35 seconds in the control measurements and is extended by the active substances. If no coagulation occurred in the measurements after 5 minutes the experiment was stopped (>300).

The measured APTT times in seconds are given in table 1 as a difference to the control. The concentrations of the active substances in the final volume were 100 μM (APTT 100), 10 μM (APTT 10), 1 μM (APTT 1), 0.1 μM (APTT 0.1).

Thrombin Time

200 μl citrate plasma is incubated for 2 minutes at 37° C. in a ball coagulometer (KC10 from the Amelung Company). 10 μl dimethylsulfoxide (DMSO) or a solution of the active substance in DMSO is added to 190 μl pre-heated thrombin reagent (Boehringer Mannheim GmbH; contains ca. 3 U/ml horse thrombin and 0.0125 M Ca⁺⁺). On addition of 200 μl of this solution to the plasma a stopwatch is started and the time at which coagulation starts is determined. The thrombin time is ca. 24 sec. in control measurements and is extended by the active substances. If no coagulation occurred in the measurements after 5 minutes the experiment was stopped (>300).

The measured thrombin times in seconds are given in table 1 as a difference to the control. The concentrations of the active substances in the final volume were 500 μM (TT 500).

Inhibition Constants

The kinetic measurements were carried out at pH=7.5 and 25° C. in 0.1 M phosphate buffer that contained 0.2 M sodium chloride and 0.5% polyethylene glycol 6000 (see below for preparation) in polystyrene semi-microcuvettes in a total volume of 1 ml. The reactions were started by addition of enzyme to pre-incubated solutions that contained either dimethyldisulfoxide (control) or solutions of the test substance in DMSO (inhibitor stock solutions: 10 mM in DMSO). The increase in absorbance at 405 nm due to the release of p-nitroaniline from the substrate was monitored over a time period of 12 minutes. Measured values (absorbance versus time) were determined at intervals of 20 seconds and these data were stored by a computer.

The inhibition constants $K_i$ were determined as follows. The rates $V_0$ (change in absorbance per second; measurements without inhibitor) and $V_i$ (change in absorbance per second; measurements with inhibitor) were determined by linear regression using only the measurement points in which the substrate concentration had decreased by less than 15%. $K_M$ and $V_{max}$ were determined from a measurement series (constant inhibitor concentration, variable substrate concentrations) by a non-linear fit to the equation $$V = \frac{V_{max} * [S]}{[S] + K_M}$$

The $K_i$ value is obtained by non-linear regression from the entire series of measurements with 16 sets of data (measurements at 4 different substrate concentrations and each with 4 different inhibitor concentrations) from the equation $$V = \frac{V_{max} * [S]}{K_M * (1 + [I]/K_i) + [S]}$$

in which $V_{Max}$ denotes the maximum rate in the absence of an inhibitor, $K_M$ denotes the Michaelis constant and [S] the substrate concentration.

The measured $K_i$ values in [μM] are stated in table 1.

FXa

Stock solution: 990 μl phosphate buffer solution (see below for preparation) was admixed with 10 μl human factor Xa (Boehringer Mannheim GmbH; 10 U; suspension) and stored on ice for a maximum of 4 hours. For the measurement 850 μl phosphate buffer and 100 μl substrate [N-methoxycarbonyl-(D)-norleucyl-glycyl-(L)-arginine-4-nitroaniline-acetate; Chromozyme X; Boehringer Mannheim GmbH; substrate concentrations used 800, 600, 400 and 200 μM; $K_M$ 400 μM] and 25 μl inhibitor solution or 25 μl DMSO (control) are preheated in a photometer (25° C.). The reaction is started by adding 25 μl stock solution.

Preparation of 0.1 M phosphate buffer solution (pH 7.5. 0.2 M NaCl)

8.90 g $Na_2HPO_4$ $H_2O$, 5.84 g NaCl and 2.50 g polyethylene glycol 6000 are dissolved in 400 ml distilled water and filled up to a total volume of 500 ml with distilled water (solution I). 1.36 g $KH_2PO_4$, 1.17 g NaCl and 0.50 g polyethylene glycol 6000 are dissolved in 80 ml distilled water and filled up to a total volume of 100 ml with distilled water (solution II). Then sufficient solution II (ca. 85 ml) is added to solution I for the pH value to be 7.5. The buffer solution is always prepared fresh (stable for a maximum of 10 days when stored in a refrigerator at 4° C.).

TABLE 1

| Pharmacological data for example compound 1 | | | | | |
|---|---|---|---|---|---|
| Example No. | Ki (fXa) | APTT 100 | APTT 10 | APTT 1 | APTT 0.1 | TT 500 |
| 1 | 0.002 | >300 | >300 | 45 | 8 | 49 |

We claim:
1. A compound of the formula

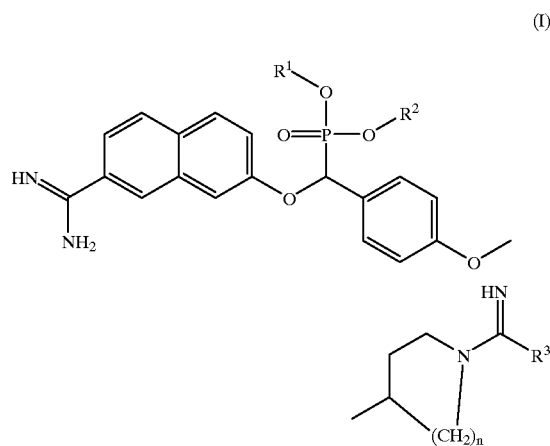

(I)

wherein
R¹ and R² are independently hydrogen, $C_1$–$C_6$ alkyl, $C_3$–$C_8$ cycloalkyl, $C_1$–$C_6$ hydroxyalkyl, $C_2$–$C_6$ alkenyl, $C_2$–$C_6$ alkinyl or aralkyl which comprises a phenyl, naphthyl or biphenyl group linked to a $C_1$–$C_6$ alkyl chain, or R¹ and R² together are an alkylene group which, together with the oxygen atoms to which it is bound and the phosphorous atom to which the oxygen atoms are bound, forms a saturated 5-membered to 8-membered ring;

R³ is (a) an amino group which is unsubstituted or substituted by at least one of $C_1$–$C_6$ alkyl, $C_3$–$C_8$ cycloalkyl, $C_1$–$C_6$ hydroxyalkyl, $C_3$–$C_6$ alkenyl, $C_3$–$C_6$ alkinyl or benzyl; (b) $C_1$–$C_6$ alkyl, (c) $C_3$–$C_8$ cycloalkyl or (d) an aryl residue selected from the group consisting of phenyl, biphenyl or naphthyl, which aryl residue is unsubstituted or substituted by at least one $C_1$–$C_6$ alkyl, $C_1$–$C_6$ alkyloxy or halogen; and n is an integer of 1 to 4;
or a pharmaceutically acceptable hydrate, solvate or salt thereof, or an optically active form thereof.

2. Compound of claim 1, wherein R¹ and R² are independently hydrogen, methyl, ethyl, propyl, alkyl, propargyl, or benzyl, or R¹ and R² together are ethylene or propylene;

R¹ is amino, N-methyl amino, N-benzyl amino, N-alkyl amino, N,N-dimethylamino, menthyl, ethyl, cyclopropyl or 4-methoxyphenyl; and n is 1 or 2.

3. Compound of claim 2, wherein R¹ and R² are both an ethyl group.

4. Compound of claim 3, wherein R¹ is a methyl group.

5. Compound of claim 1, wherein the compound is ((7-carbamimidoyl-naphthalen-2-yloxy)-{4-[1-(1-iminoethyl)-piperidin-4-yloxy]-phenyl}-methyl)-phosphonic acid diethyl ester-dihydrochloride.

6. Pharmaceutical composition suitable for inhibiting factor Xa, comprising a factor Xa-inhibiting effective amount of a compound of claim 1 and a pharmaceutically acceptable carrier therefor.

7. A method for the treatment or prophylactic treatment of thrombosis, apoplexy, coronary infarction, inflammation or arteriosclerosis in a patient in need of such treatment or prophylactic treatment, comprising administering an effective amount of a compound of claim 1 to the patient.

8. A method of inhibiting factor Xa in a patient in need of such inhibition, said method comprising administering a factor Xa-inhibiting amount of a compound of claim 1 to the patient.

9. A method of preventing the formation of hyaline thrombi in a patient in need of such prevention, comprising administering to said patient a hyaline thrombi-preventing amount of a compound of claim 1.

10. Method of claim 7, wherein the compound is ((7-carbamimidoyl-naphthalen-2-yloxy)-{4-[1-(1-iminoethyl)-piperidin-4-yloxy]-phenyl}-methyl)-phosphonic acid diethyl ester-dihydrochloride.

11. Method of claim 8, wherein the compound is ((7-carbamimidoyl-naphthalen-2-yloxy)-{4-[1-(1-iminoethyl)-piperidin-4-yloxy]-phenyl}-methyl)-phosphonic acid diethyl ester-dihydrochloride.

12. Method of claim 9, wherein the compound is ((7-carbamimidoyl-naphthalen-2-yloxy)-{4-[1-(1-iminoethyl)-piperidin-4-yloxy]-phenyl}-methyl)-phosphonic acid diethyl ester-dihydrochloride.

\* \* \* \* \*